United States Patent [19]

Mease et al.

[11] Patent Number: 5,635,157

[45] Date of Patent: Jun. 3, 1997

[54] SYNTHESIS OF 4-SUBSTITUTED-TRANS-1,2-DIAMINOCYCLOHEXYL POLYAMINOCARBOXYLATE METAL CHELATING AGENTS FOR THE PREPARATION OF STABLE RADIOMETAL ANTIBODY IMMUNOCONJUGATES FOR THERAPY AND SPECT AND PET IMAGING

[76] Inventors: Ronnie C. Mease, 2101 B. Ulster Pl., Coram, N.Y. 11727; Kathryn L. Kolsky, 460 Harrison Ave., Miller Pl., N.Y. 11764; Leonard F. Mausner, 16 Seville Ln., Stony Brook, N.Y. 11790; Suresh C. Srivastava, 8 Penelope Dr., Setauket, N.Y. 11733

[21] Appl. No.: 132,201

[22] Filed: Oct. 6, 1993

Related U.S. Application Data

[62] Division of Ser. No. 867,533, Apr. 13, 1992, Pat. No. 5,292,938.

[51] Int. Cl.$^6$ .................. A61K 51/08; A61K 51/10
[52] U.S. Cl. .............. 424/1.53; 424/169; 530/391.5; 534/10; 534/14
[58] Field of Search ............... 424/1.49, 1.65, 424/1.69, 1.53, 1.45; 534/10, 14; 530/391.5

[56] References Cited

U.S. PATENT DOCUMENTS

| | | | |
|---|---|---|---|
| 4,707,352 | 11/1987 | Stavrianpoulos | 424/1.1 |
| 4,707,440 | 11/1987 | Stavrianpoulos | 435/6 |
| 4,767,609 | 8/1988 | Stavrianpoulos | 424/1.1 |
| 4,849,208 | 7/1989 | Stavrianpoulos | 424/1.1 |
| 5,021,571 | 6/1991 | Mease et al. | 544/166 |
| 5,089,663 | 2/1992 | Mease et al. | 562/507 |
| 5,260,433 | 11/1993 | Engelhardt et al. | 536/23.1 |
| 5,286,850 | 2/1994 | Giansoh et al. | 424/1.45 |
| 5,334,729 | 8/1994 | Mease et al. | 548/546 |

FOREIGN PATENT DOCUMENTS 097373   1/1984   European Pat. Off. .

OTHER PUBLICATIONS

Fischman et al., *J. Nuc. Med.*, vol. 34, No. 12, Dec. 1993, pp.2253–2263.
Aldrich Product Catalogue, 1993, p.435.
Mease et al., "Effect of Chelate Rigidity...", *J. Label. Comp. and Radiopharm.*, 30, 1991, pp.319–321.
Srivastava et al., "CDTA –In –111 –Anti –CEA F(ab')2 Immunoconjugates", *Suppl. to J. Nuc. Med.*, 32(5), 1991, p.1023, Ab. #480.
Mease et al., "Synthesis and Evaluation...", *Suppl. to J. Nuc. Med.*, 32(5), 1991, p. 1023, Ab #482.

*Primary Examiner*—John Kight
*Assistant Examiner*—Lara Chapman Kelley
*Attorney, Agent, or Firm*—M. C. Bogosian

[57] ABSTRACT

Cyclohexyl chelating agents useful in forming antibody-metal conjugates useful for diagnostic and therapeutic purposes. New compounds and processes of forming these compounds are disclosed including 4-haloacetamido-trans-1,2-diaminocyclohexyl polyaminocarboxylate and 4-isothiocyanato-trans-1,2-diamino cyclohexane-N, N, N', N'-tetra acetic acid.

17 Claims, No Drawings

SYNTHESIS OF 4-SUBSTITUTED-TRANS-1,2-DIAMINOCYCLOHEXYL POLYAMINOCARBOXYLATE METAL CHELATING AGENTS FOR THE PREPARATION OF STABLE RADIOMETAL ANTIBODY IMMUNOCONJUGATES FOR THERAPY AND SPECT AND PET IMAGING

RELATED APPLICATIONS

This is a divisional of application Ser. No. 07/867,533 filed Apr. 13, 1992, and now U.S. Pat. No. 5,292,938 issued Mar. 8, 1994.

This invention was made with Government support under contract number DE-AC02-76CH00016, between the U.S. Department of Energy and Associated Universities, Inc. The Government has certain rights in the invention.

BACKGROUND OF THE INVENTION

This present invention relates to the synthesis and evaluation of cyclohexyl chelating agents where the complexation of radiometals occurs on one side of the cyclohexane ring and the other side of the ring contains a moiety which allows the chelating agent to be attached to proteins such as antibodies and peptides. By the proper choice of radiometal and antibody these antibody-metal conjugates can be used for diagnostic imaging or therapy.

The use of radiometals to label proteins and antibodies provides a wealth of choices of half-life and emissions for various applications (diagnosis and therapy). In addition, radiometal labeling avoids the deleterious oxidation effects experienced in direct iodination reactions. Labeling with metals can also overcome problems of in-vivo deiodination by tumor and normal tissues, particularly when using rapidly internalized antibodies.

Radiometals can generally be attached to antibodies by the use of a "bifunctional chelate" which is first covalently attached to the antibody to form an antibody-chelate conjugate and then bound to the radiometal. The early work in this field used diethylenetriaminepentaacetic acid (DTPA) and its derivatives. This compound has a backbone consisting of three nitrogens separated by two ethylene bridges. The two terminal amine groups each contain two carboxymethyl groups while the internal amine contains one carboxymethyl group. DTPA is generally conjugated to antibodies via its bicyclic anhydride (DTPADA) which forms a covalent amide bond between an antibody amine and one of the carboxylic acid groups of DTPA [Hnatowich, et al. Science 220, 613 (1983)]. This method while convenient has drawbacks. For example, with indium-111 this procedure yields high liver retention and slow body clearance [Goodwin, J. Nucl. Med. 28, 1358 (1987)], as well as a substantial amount of crosslinked antibody (two antibodies linked together by a DTPA bridge). This crosslinking can reduce the immunoreactivity of the antibody, increase liver retention, and decrease tumor uptake.

The introduction of benzyl groups onto the backbone of EDTA and DTPA has been shown to increase the serum stability of $^{111}$In-benzyl EDTA and -benzyl DTPA chelates and antibody conjugates and to decrease the retention of indium in the liver of nude tumor mice [Cole, et al. Nucl. Med. Biol. 13, 363 (1980)]. Unfortunately, this reduction in the retention of indium in the liver has not been observed in patients using these chelating agents [Hnatowich, Seminars in Nucl. Med. 20, 80 (1990)]. With yttrium-88 benzyl-DTPA conjugates were more stable thereby giving higher tumor uptake and lower bone retention than the benzyl-EDTA or cyclic DTPA conjugates [Roselli, et al. J. Nucl. Med. 24, 932 (1989)] in nude tumor mice. The above benzyl-EDTA and benzyl-DTPA ligands where attached to antibodies via 4-isothiocyanato benzyl or a 4-bromoacetamido-benzyl group thereby freeing all five carboxylates for metal complexation. Chelating agents which contain a cyclic backbone are also useful for attaching radiometals to antibodies. For example, the use of macrocyclic polyaminocarboxylates such as the bromoacetamido derivatives of 6-(p-aminobenzyl)-1,4,8,11-tetraazacyclotetradecane-N,N',N",N'"-tetraacetic acid [Moi et al., Anal. Biochem 148, 249 (1985)] or 2-(p-aminobenzyl)-1,4,7,10-tetraazacyclododecane-N,N',N",N'" tetraacetic acid [Moi et al., J. Am. Chem. Soc. 110, 6266 (1988)] have both produced stable copper conjugates while the latter produced stable yttrium conjugates [Deshpande et al., J. Nucl. Med. 31, 473 (1990). The isothiocyanato derivative of the latter compound prepared by a different route has produced stable bismuth conjugates [Gansow and Kumar, U.S. Pat. No. 4,923,985 (1990)].

Trans-1,2-diaminocyclohexane-N,N,N',N'-tetraacetic acid (CDTA) is a strong general purpose chelating agents for complexing metals. Its thermodynamic stability constants are generally 1–3 orders of magnitude greater than ethylenediamine tetraacetic acid (EDTA) [Martell and Smith, Critical Stability Constants, Vol. 1., Plenum Press, NY, 1974]. CDTA has been used to remove heavy metals from the body [Kroll et al., Nature 180, 919 (1957)]. To attach CDTA to proteins such as antibodies, CDTA has been converted to its monoanhydride (CDTAMA) [Mease and Svivastava, U.S. Pat. No. 5,021,571 (1991)]. Since CDTAMA is monofunctionalized it does not produce any crosslinked antibodies. $^{111}$In, $^{57}$Co, and $^{97}$Ru labeled immunoconjugates prepared using CDTAMA have shown promising biodistributions in mice. Higher denticity chelating agents containing the cyclohexane ring such as N,N'-(2-aminoethyl)-trans-1,2-diaminocyclohexane-N,N',N",N'",N'",N'"-hexaacetic acid (CTTHA) have been prepared and conjugated to antibodies by converting two of the acid groups to activated N-hydroxy succinimide esters [Mease et al. U.S. Pat. No. 5,089,663 (1992)]. In the above cyclohexyl chelating agents, all attachments to the antibody have been through one of the carboxylate groups. This eliminates one coordination group from the ligand and this loss may become critical when trying to complex metals which prefer high coordination numbers. The disclosure of Johnson D. K. (European Patent Application 88101776.8 (1988)) presents a method of attaching a p-nitrobenzyl group to the carbon alpha to one of the carboxyl groups of CDTA to produce N-(carboxymethyl)-N-(trans-2-(bis(carboxymethyl)amino)cyclohexyl))-(4-nitrophenyl)alanine. Although not presented in that European application, for this particular compound the

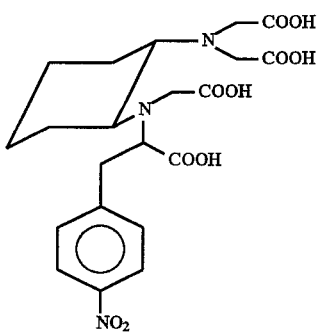

4-nitro group can be reduced to a primary amine and converted to an isothiocyanato group for immunoconjugation. While a reasonable method, this approach is only general for the production of polyaminocarboxylate ligands and the juxtaposition of the benzyl cyclohexyl groups may sterically inhibit metal complexation.

In order to move the conjugating moiety to the other side of the cyclohexane ring, Stavrianopoulos (U.S. Pat. No. 4,707,440 (1987)) has prepared the bromohydrin compound 1

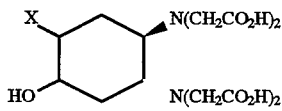

1 x=—Br
2 x=—SCH$_2$CH$_2$C(O)NHNH$_2$
3 x=—SC$_6$H$_6$NH$_2$

This was converted to 5-hydroxy-CDTA-4-B-thioproprionic acid hydrazide 2. This was conjugated to BSA using 1M HCl and 1M NaNO$_2$. Also the 4-aminophenyl derivative 3 was prepared and conjugated to BSA by the formation of a very reactive diazonium salt. While demonstrating the ability of attaching CDTA to a protein on the back side of CDTA the methods described are not convenient and may not be applicable to sensitive antibodies.

4-amino CDTA is describe briefly in the disclosure of Engelhardt et al. (European Patent Application #83106112.2). No details of this preparation which starts with 1-hydroxy-3,4-dinitro benzene are given. Also no stereochemistry is given on the reduction product 4-hydroxy-1,2-diaminocyclohexane or subsequent intermediates including 4-amino CDTA. The diamines must be in the trans-diequatorial position for effective metal complexation.

SUMMARY OF THE INVENTION

Aspects of the present invention relate to novel compounds and novel processes for the formation of novel cyclohexyl chelating agents, as well as useful intermediates formed during those processes. Included in the present invention are novel processes for the formation of 4-haloacetamido-trans-1,2-diaminocyclohexyl polyaminocarboxylate and 4-isothiocyanato-trans-1,2-diamino cyclohexane-N, N, N', N'-tetra acetic acid.

Radioimmunoconjugates of the present invention show higher and prolonged tumor uptake with lower retention in kidneys, bones and livers.

The cyclohexyl chelating agents of the present invention are useful for diagnostic procedures including planar imaging, SPECT IMAGING, PET IMAGING, as well as in therapeutic procedures.

DETAILED DESCRIPTION OF THE INVENTION

The present invention is directed to the preparation of new forms and derivatives of the semi-rigid chelates trans-1,2-diaminocyclohexane-N,N,N',N'-tetraacetic acid (CDTA), N-(2-aminoethyl)-trans-1,2-diaminocyclohexane-N,N',N', N'',N''-pentaacetic acid (CDTPA) and N,N'-(2-aminoethyl)-trans-1,2-diaminocyclohexane-N,N',N'',N'',N''',N'''-hexaacetic acid (CTTHA).

In particular, the present invention comprises methods for the production of 4-substituted-trans-1,2-diamino cyclohexane-N,N,N',N'-tetraacetic acid depicted by the formula

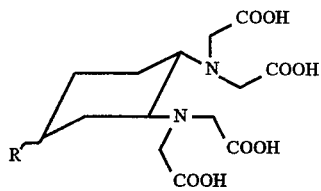

wherein R is
—NH$_2$
—N=C=S
—NHC(O)CH$_2$X where X=Cl, Br, or I
and useful intermediates formed by these methods. In particular 4-amino CDTA (i.e., R=NH$_2$) has been prepared by two routes. In the first route (Scheme 1) trans-1,2-diaminocyclohex-4-ene 4 was prepared by a modification of the procedure of Witiak et al. [J. Med. Chem. 30, 1327 (1987)]. This was alkylated with bromoacetic acid to give tetraacid 5. To convert 5 into a form which would dissolve in normal organic solvents, 5 was esterified using boron-trifluoride etherate in ethanol to give tetraester 6. The double bond of 6 underwent a mercuration-amidation reaction with mercuric nitrate in acetonitrile followed by a basic NaBH$_4$ workup to produce 7 with an acetamide group on carbon-4. Hydrolysis of the ester and amide groups of 7 produced 4-amino DTA 8. In the second route (Scheme 2) trans-1,2-diaminocyclohex-4-ene 4 is first converted to the dicarbonate 9. This is followed by mercuration-amidation to give 10. Mild hydrolysis of 10 produced 11 which was alkylated using ethyl bromoacetate to give tetra ester 12. Hydrolysis of both the amide and ester groups produced 4-amino CDTA 8. It is noteworthy that compound 11 contains two different types of amine groups. The primary amines on carbons one and two are available for either alkylation to form a polyaminocarboxylate-metal complexing group as in 8 or other chelating groups containing two nitrogens. One or both of these nitrogens can also be alkylated to expand the carbon chain to increase the denticity of the ligand. The third amine is masked as an amide which can be hydrolyzed at the end of the synthesis to produce a primary amine for functionalization as a isothiocyanate or a bromoacetamide.

Tetra acid 8 was converted to its tetra lithium salt by contacting the tetra acid 8 with five equivalents of LiOH, drying, dissolving in methanol and reacting with thiophosgene in methanol to give 4-isothiocyanato-trans-1,2-diaminocyclohexane-N,N,N',N'-tetra acetic acid dilithium salt (4-ICE). In our hand, the procedure of DeRiemer [J. Labelled Compd. Radiopharm 18, 1517 (1981)] also failed to produce the desired bromoacetamide. Instead 4-amino CDTA 8 was reacted with N-hydroxysuccinimidyl bromoacetate and pentamethylpiperidine to give 4-bromoacetamido-trans-1,2-diaminocyclohexane-N,N,N',N'-tetraacetic acid (4-BACE).

Synthesis of 4AminoCDTA, 4-ICE and 4-BACE
Scheme 1
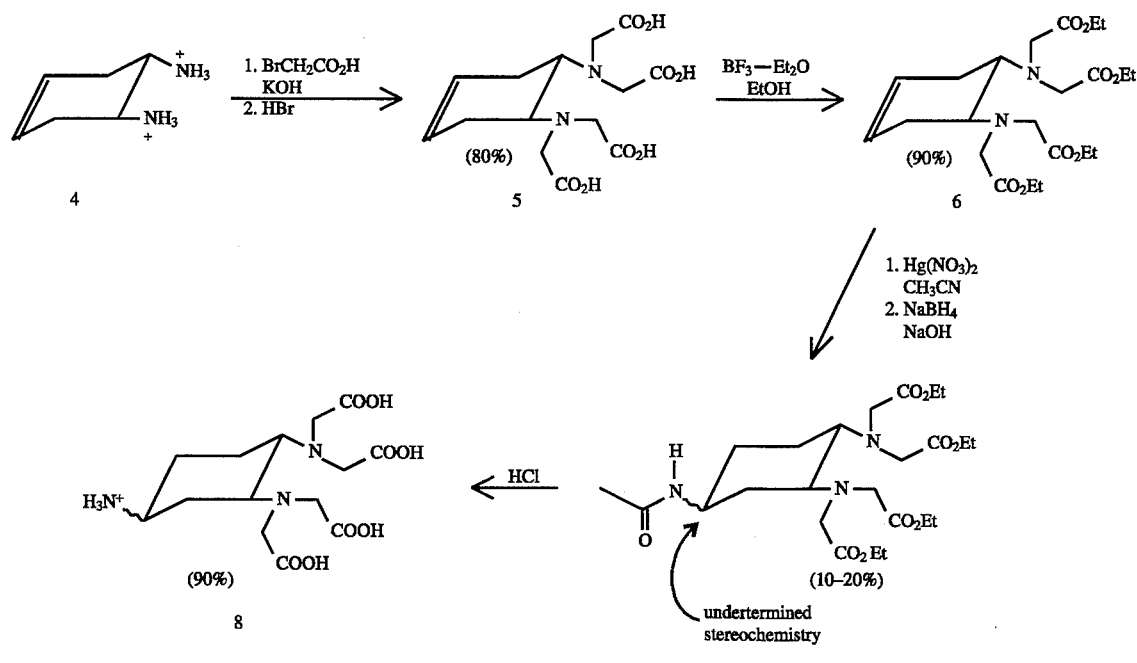
Scheme 2
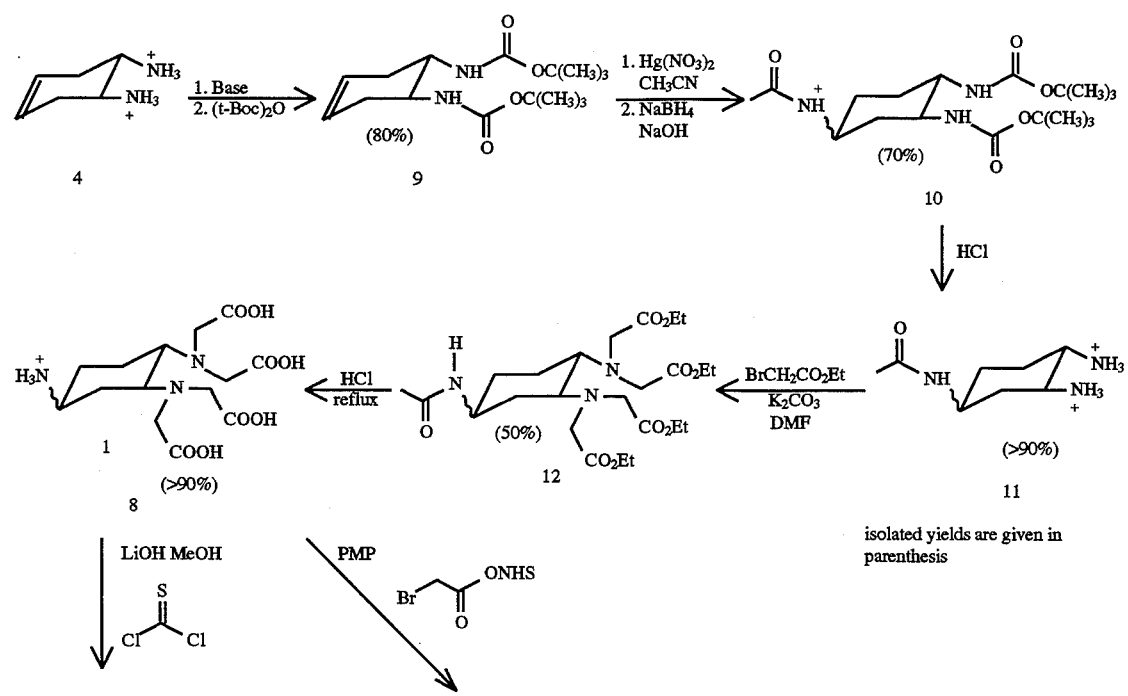
isolated yields are given in parenthesis -continued
Scheme 2

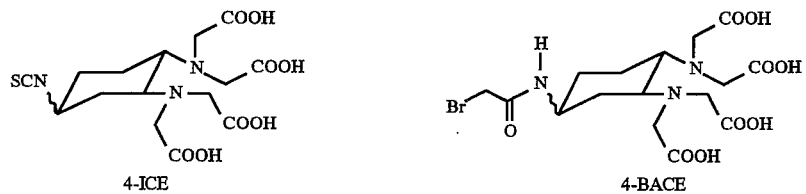

4-ICE, 4-BACE, CDTAMA, and DTPADA were conjugated to anticolon carcinoma antibody 17-1A IgG, labeled with $^{111}$In and purified by size exclusion HPLC to remove any crosslinked antibody (only present when DTPADA was used). 25 µg of the labeled preparation was injected into normal mice. The biodistribution at 24H and 96H is given in Table 1. 4-ICE and 4-BACE immunoconjugates both have lower liver and bone retention than either CDTAMA or DTPADA immunoconjugates and lower kidney retention than DTPADA immunoconjugates. In nude mice bearing SW948 tumor xerografts $^{111}$In labeled 17-1A 4-ICE and 4-BACE showed higher and prolonged tumor uptake compared to CDTAMA and DTPADA (Table 2). Kidney and bone retention for 4-ICE and 4-BACE are lower than that of CDTAMA and DTPADA. While all of these conjugates have similar liver retention, part of the uptake of the 4-ICE and 4-BACE conjugates could be due to the prolonged blood retention of the 4-ICE, 4-BACE-IgG conjugates. Tumor/organ ratios from this biodistribution are given in Table 3. 4-ICE and 4-BACE conjugates clearly show higher tumor/liver, tumor/kidney and tumor/bone ratios than CDTAMA and DTPADA. However, tumor/blood ratios are lower due to the prolonged blood retention of 4-ICE/4-BACE. If this prolonged blood retention is due to the antibody itself and not the transfer of the $^{111}$In to a component in the blood then the use of an antibody fragment should help speed blood clearance of the $^{111}$In.

TABLE 1

Tissue Distribution in Normal Mice of
17-1A IgG Conjugates Labeled with $^{111}$In[a]

| Bifunctional Chelating Agent | Time (H) | Blood | Liver | Kidney | Bone | Whole[b] Body |
|---|---|---|---|---|---|---|
| DTPADA | 24 | 10.6 | 13.4 | 11.2 | 5.4 | 98 |
|  | 96 | 3.6 | 9.5 | 6.7 | 4.6 | 60 |
| CDTAMA | 24 | 15.7 | 10.2 | 5.5 | 3.4 | 95 |
|  | 96 | 10.4 | 6.9 | 4.3 | 2.4 | 64 |
| 4-ICE | 24 | 18.4 | 5.9 | 4.9 | 2.7 | 92 |
|  | 96 | 13.1 | 6.6 | 3.9 | 2.0 | 71 |
| 4-BACE | 24 | 18.4 | 6.3 | 5.3 | 2.9 | 91 |
|  | 96 | 10.1 | 5.6 | 3.8 | 1.7 | 67 |

[a]Data (% DOSE g$^{-1}$) normalized to 25 g body wt; purification carried out by HPLC using Zorbax GF-250 column; n = 3.
[b]Percent injected dose retained.

TABLE 2

Tissue Distribution in Nude Tumor Mice
of 17-1A IgG Conjugates Labeled with $^{111}$In[a]

| Bifunctional Chelating Agent | n | Time | Tumor | Blood | Liver | Kidney | Bone | Whole[b] Body |
|---|---|---|---|---|---|---|---|---|
| 4-ICE | 3 | 24 | 17.6 | 20.6 | 8.0 | 5.3 | 2.3 | 100 |
|  | 2 | 96 | 20.0 | 8.4 | 6.5 | 3.8 | 1.3 | 75 |
| 4-BACE | 4 | 24 | 14.0 | 13.4 | 6.6 | 3.4 | 1.8 | 92 |
|  | 3 | 96 | 17.3 | 5.9 | 7.7 | 2.9 | 1.1 | 70 |
| CDTAMA[c] | 4 | 24 | 14.0 | 4.2 | 9.0 | 4.2 | 6.0 | 98 |
|  | 4 | 96 | 6.0 | 1.0 | 7.5 | 4.3 | 2.5 | 75 |
| DTPADA[c] | 6 | 24 | 11.2 | 5.6 | 8.8 | 8.8 | 5.2 | 96 |
|  | 6 | 96 | 9.8 | 2.6 | 6.5 | 11.6 | 3.6 | 71 |

[a]DATA (% does g$^{-1}$) normalize to 25 g body wt; purification carried out by HPLC using Zorbax GF-250 column.
[b]Percent injected dose retained.
[c]Data from Table 2, U.S. Pat. No. 5,089,663.

TABLE 3

Tumor T/Tissue Ratios of Indium-111 Labeled 17-1A IgG Conjugates in Nude Tumor Mice

| Bifunctional Chelating Agent | Time (H) | n | T/Blood | T/Liver | T/Kidney | T/Bone |
|---|---|---|---|---|---|---|
| 4-ICE | 24 | 3 | 0.9 | 2.2 | 3.3 | 7.7 |
|  | 96 | 2 | 2.4 | 3.1 | 5.3 | 15 |
| 4-BACE | 24 | 4 | 1.0 | 2.1 | 4.2 | 7.8 |
|  | 96 | 3 | 2.9 | 2.2 | 6.0 | 15 |
| CDTAMA[a] | 24 | 4 | 3.3 | 1.6 | 3.3 | 2.3 |
|  | 96 | 4 | 6.0 | 0.8 | 1.4 | 2.4 |
| DTPADA[a] | 24 | 6 | 2.0 | 1.3 | 1.3 | 2.1 |
|  | 96 | 6 | 3.8 | 1.5 | 0.8 | 2.7 |

[a]Data from Table 3, U.S. Pat. No. 5,089,663.

The biodistribution in Table 4 and Tumor/organ ratios in Table 5 clearly show that this is the case. Using the F(ab')$_2$ fragment of anti-CEA, the $^{111}$In labeled preparations using 4-ICE and 4-BACE have lower blood, liver, and bone uptake at 24H compared to DTPADA. At later time (96H), 4-ICE and 4-BACE also have lower kidney retnetion. At both points in time the tumor uptake was similar for all preparations. This leads to 4-ICE and 4-BACE having generally higher tumor/blood, tumor/liver, tumor/kidney, and tumor/bone ratios.

Scandium-47 has a half-life of 3.35 days, intermediate energy beta emissions [441.1 KeVmax (68%), 600.5 KeVmax (32%)] and an imageable gamma emmission [159.4 KeV[KeV]]. The intermediate energy beta emissions make $^{47}$Sc attractive for radioimmunotherapy while the imageable gamma ray allows imaging studies to be performed prior to therapy to confirm tumor localization of the radioactivity. Early work with $^{46}$Sc labeled antibodies using DTPADA showed instability in serum in-vitro as well as substantial uptake in the liver, muscle, and intestine in mice [Anderson and Strand Cancer Research 45,2154 (1985)]. The distribution of $^{47}$Sc labeled 17-1A IgG preparations prepared using 4-ICE, CDTAMA, and DTPADA is given in Table 6. 4-ICE conjugates have lower liver, kidney and bone uptake compared to CDTAMA or DTPADA. 4-ICE conjugates also have prolonged blood retention. In fact, the biodistribution of $^{47}$Sc labeled 4-ICE-17-1A conjugates is almost identical to that of $^{111}$In labeled 4-ICE-17-1A. This is what one would expect if the radiolabel is sufficiently bound to the antibody so that only the distribution of the antibody determines the distribution of the radiolabel. Table 7 lists the biodistribution in SW 948 xenografted nude mice of $^{47}$Sc labeled 4-ICE and DTPADA conjugated 17-1A IgG. 4-ICE conjugates have higher tumor uptake with longer blood retention than DTPADA conjugates. 4-ICE conjugates also have lower liver uptake than DTPADA conjugates. As in normal mice the biodistribution of $^{111}$In -4-ICE-17-1A conjugates in nude mice bearing tumor xenografts (Table 2) is similar to the biodistribution of $^{47}$Sc-4-ICE-17-1A (Table 7). $^{47}$Sc-4-ICE-17-1A conjugates produce higher T/liver, T/kidney, and T/bone ratios than $^{47}$Sc DTPADA-17-1A conjugates (Table 8). The lower T/blood ratio of 4-ICE conjugates compared to DTPA-conjugates is again probably due to the slow clearance of the 17-1A IgG.

TABLE 4

Tissue Distribution in Nude Tumor Mice of Anti-CEA F(ab')$_2$ Conjugates Labeled with Indium-111[a]

| Bifunctional Chelating Agent | Time | n | Tumor | Blood | Liver | Kidney | Bone | Whole[b] Body |
|---|---|---|---|---|---|---|---|---|
| 4-ICE | 24 | 7 | 15.1 | 3.0 | 5.3 | 11.1 | 1.0 | 63 |
|  | 96 | 8 | 8.5 | 0.095 | 2.2 | 2.5 | 0.4 | 18 |
| 4-BACE | 24 | 5 | 12.7 | 1.9 | 9.2 | 11.3 | 0.9 | 75 |
|  | 96 | 5 | 7.7 | 0.05 | 3.2 | 5.2 | 0.5 | 39 |
| DTPADA | 24 | 3 | 13.2 | 6.5 | 11.0 | 11.2 | 1.8 | 68 |
|  | 96 | 3 | 9.8 | 0.5 | 7.3 | 6.7 | 1.8 | 46 |

[a]Data (% dose g$^{-1}$) normalized to 25 g body wt; purification carried out by HPLC using Zorbax GF-250 column.
[b]Percent injected dose retained.

TABLE 5

Tumor (T)/Tissue Ratios of Indium-111 Labeled Anti-CEA F(ab')$_2$ Conjugates in Nude Tumor Mice

| Bifunctional Chelating Agent | Time (H) | n | T/Blood | T/Liver | T/Kidney | T/Bone |
|---|---|---|---|---|---|---|
| 4-ICE | 24 | 7 | 5 | 2.8 | 1.4 | 15.1 |
|  | 96 | 8 | 89 | 3.9 | 3.4 | 21 |
| 4-BACE | 24 | 5 | 6.5 | 1.4 | 1.1 | 14.6 |
|  | 96 | 5 | 148 | 2.4 | 1.5 | 15 |
| DTPADA | 24 | 3 | 2.0 | 1.2 | 1.2 | 7.5 |
|  | 96 | 3 | 21 | 1.3 | 1.5 | 5.4 |

TABLE 6

Tissue Distribution in Normal Mice of
17-1A IgG Conjugates Labeled with $^{47}$Sc[a]

| Bifunctional Chelating Agent | Time (H) | Blood | Liver | Kidney | Bone | Whole[b] Body |
|---|---|---|---|---|---|---|
| 4-ICE | 24 | 17.9 | 8.5 | 5.0 | 2.3 | 94 |
|  | 96 | 12.0 | 8.2 | 4.6 | 2.5 | 82 |
| CDTAMA | 24 | 8.2 | 17.3 | 6.5 | 3.5 | 94 |
|  | 96 | 2.9 | 20.5 | 4.7 | 3.0 | 82 |
| DTPADA | 24 | 3.9 | 13.8 | 6.2 | 3.6 | 90 |
|  | 96 | 0.7 | 15.7 | 5.2 | 3.6 | 73 |

[a]Data (% dose g$^{-1}$) normalized to 25 g body wt; purification carried out by HPLC using Zorbax GF-250 column; n = 3.
[b]Percent injected dose retained.

As a model for the use of $^{55}$Co (T$_{1/2}$ 18.2H) labeled antibodies for PET imaging of tumors, $^{57}$Co has been used in biodistribution studies in mice. Previous work has shown that the use of CDTAMA-17-1A conjugates produce more stable $^{57}$Co conjugates in serum in-vitro than DTPADA-17-1A conjugates [Mease et al., U.S. Pat. No. 5,089,663]. $^{57}$Co labeled CDTAMA-17-1A conjugates showed higher tumor uptake than $^{57}$Co labeled DTPADA-17-1A. The distribution in nude mice bearing SW 948 tumor xenografts of $^{57}$Co labeled 4-ICE- and 4-BACE-17-1A IgG is given in Table 9 along with an earlier experiment with CDTAMA and DTPADA. Compared to DTPADA conjugates, the 4-ICE and 4-BACE conjugates give higher tumor uptake with prolonged blood retention similar to what was observed with $^{111}$In and $^{47}$Sc labeled 4-ICE/4-BACE conjugates and shown in Tables 2 and 7, respectively. The distribution of 4-ICE, 4-BACE, and CDTAMA conjugates at 24H were all quite similar with high tumor uptake and high blood retention. The distributions were not similar at 96H where the uptake of 4-BACE-17-1A increased in the tumor while CDTAMA-17-1A cleared faster from both the tumor and blood. This difference is also reflected in the serum stability of the respective conjugates in serum. The loss of $^{57}$Co from 4-ICE/4-BACE-17-1A was 1–4% at both 24 and 96H while the loss of $^{57}$Co from CDTAMA-17-1A was 4% at 24H which increased to 59% at 96H. Tumor to organ ratios are given in Table 10. At 24H, despite the high tumor uptake and high T/Liver, T/kidney, and T/bone ratios for the 4-ICE/4-BACE conjugates, the low T/blood ratio would probably not produce a contrast sufficient for PET Imaging (T/Blood needs to be $\geq 2$). Acceptable ratios are achieved at 96H for 4-BACE-17-1A IgG but 96H is probably too long for the 17H half life of $^{55}$Co. Therefore, antibody fragments with their faster blood clearance are needed to achieve the ratios needed for PET imaging.

TABLE 7

Tissue Distribution in Nude Tumor Mice
of 17-1A IgG Conjugates Labeled with $^{47}$Sc[a]

| Bifunctional Chelating Agent | Time (H) | Tumor | Blood | Liver | Kidney | Bone | Whole[b] Body |
|---|---|---|---|---|---|---|---|
| 4-ICE | 24 | 8.1 | 14.1 | 5.5 | 3.5 | 2.5 | 80 |
|  | 96 | 13.4 | 11.3 | 5.3 | 3.4 | 2.6 | 72 |
| DTPADA | 24 | 6.4 | 10.3 | 8.7 | 3.8 | 3.0 | 86 |
|  | 96 | 6.2 | 1.8 | 7.6 | 4.2 | 2.8 | 66 |

[a]Data (% dose g$^{-1}$) normalized to 25 g body wt; purification carried out by HPLC using Zorbax GF-250 column, n = 5.
[b]Percent injected dose retained.

TABLE 8

Tumor (T)/Tissue Ratios of Scandium-47 Labeled
17-1A IgG Conjugates in Nude Tumor Mice[a]

| Bifunctional Chelating Agent | Time (H) | T/Blood | T/Liver | T/Kidney | T/Bone |
|---|---|---|---|---|---|
| 4-ICE | 24 | 0.6 | 1.5 | 2.3 | 3.2 |
|  | 96 | 1.2 | 2.5 | 4.0 | 5.1 |
| DTPADA | 24 | 0.6 | 0.7 | 1.7 | 2.1 |
|  | 96 | 3.5 | 0.8 | 1.5 | 2.2 |

[a]n = 5

The tissue distribution in nude mice with LS 174 T xenografts of $^{57}$Co labeled 4-ICE and 4-BACE anti-CEA F(ab')$_2$ conjugates is given in Table 11. The $^{57}$Co labeled 4-ICE and 4-BACE anti-CEA F(ab')$_2$ conjugates are comparable to each other and to the distribution of $^{111}$In labeled 4-ICE and 4-BACE anti-CEA F(ab')$_2$ conjugates with the exception that the $^{57}$Co 4-ICE/4-BACE preparations have lower kidney retention. The tumor/tissue ratios are given in Table 12. Both 4-ICE and 4-BACE anti-CEA F(ab')$_2$ conjugates give T/blood, T/liver, T/kidney, and T/bone ratios that are acceptable for imaging as early as 24H. This is well within the useful life of $^{55}$Co (T½ 17H).

In order to evaluate the usefulness of these CDTA derivatives with metals that prefer coordination numbers greater than 6, 4-ICE-17-1A IgG conjugates were labeled with $^{88}$Y and $^{203}$Pb, respectively, and evaluated in SW 948 xenografted nude mice (Table 13). Compared to $^{88}$Y labeled DTPADA-17-1A IgG conjugates, 4-ICE-17-1A IgG conjugates had higher tumor uptake with lower liver uptake. Unfortunately, the bone uptake was not reduced. Therefore, while producing an improvement over DTPADA, the use of 4-ICE does not give a better distribution than either the p-aminobenzyl derivatives of DTPA or DOTA. The distribution of $^{203}$Pb labeled 4-ICE-17-1A IgG (Table 14) shows low tumor uptake with high kidney and bone retention.

Clearly 4-ICE is not a suitable bifunctional chelating agent for metals like yttrium and lead which require coordination numbers greater than six.

TABLE 9

Tissue Distribution in Nude Tumor Mice
17-1A IgG Conjugates Labeled with $^{57}$Co[a]

| Bifunctional Chelating Agent | Time | n | Tumor | Blood | Liver | Kidney | Bone | Whole[b] Body |
|---|---|---|---|---|---|---|---|---|
| 4-ICE | 24 | 3 | 13.5 | 13.4 | 5.6 | 3.4 | 1.7 | 97 |
| 4-BACE | 24 | 3 | 14.6 | 17.4 | 6.7 | 3.9 | 1.7 | 90 |
|  | 96 | 3 | 17.1 | 8.2 | 4.2 | 2.7 | 1.1 | 65 |
| CDTAMA[c] | 24 | 5 | 12.8 | 12.9 | 5.7 | 3.5 | 2.5 | 79 |
|  | 96 | 5 | 4.1 | 1.5 | 2.7 | 1.9 | 1.4 | 31 |
| DTPADA[c] | 24 | 6 | 5.6 | 2.2 | 5.8 | 3.6 | 1.9 | 41 |
|  | 96 | 7 | 0.9 | 0.4 | 2.2 | 1.6 | 0.6 | 10 |

[a]Data (% dose g$^{-1}$) normalized to 25 g body wt; purification carried out by HPLC using Zorbax GF-250 column.
[b]Percent of injected dose retained.
[c]Data from Table 8, U.S. Pat. No. 5,089,663.

TABLE 10

Tumor (T)/Tissue Ratios of Cobalt-57 Labeled
17-1A IgG Conjugates in Nude Tumor Mice

| Bifunctional Chelating Agent | Time (H) | n | T/ Blood | T/ Liver | T/ Kidney | T/ Bone |
|---|---|---|---|---|---|---|
| 4-ICE | 24 | 3 | 1.0 | 2.4 | 4.0 | 8 |
| 4-BACE | 24 | 3 | 0.84 | 2.2 | 3.7 | 8.4 |
|  | 96 | 3 | 2.1 | 4.1 | 6.4 | 15.7 |
| CDTAMA | 24 | 5 | 1.0 | 2.2 | 3.7 | 5.1 |
|  | 96 | 5 | 2.7 | 1.5 | 2.1 | 2.9 |
| DTPADA | 24 | 6 | 2.5 | 1.0 | 1.5 | 2.9 |
|  | 96 | 7 | 2.25 | 0.4 | 0.6 | 1.5 |

TABLE 11

Tissue Distribution in Nude Tumor Mice
of Anti-CEA F(ab')$_2$ Conjugates Labeled with $^{57}$Co[a]

| Bifunctional Chelating Agent | Time (H) | Tumor | Blood | Liver | Kidney | Bone | Whole[b] Body |
|---|---|---|---|---|---|---|---|
| 4-ICE | 24 | 13.1 | 3.0 | 4.4 | 6.3 | 0.9 | 57 |
|  | 96 | 6.7 | 0.15 | 1.6 | 1.7 | 0.3 | 21 |
| 4-BACE | 24 | 11.6 | 2.9 | 5.8 | 6.9 | 0.9 | 55 |
|  | 96 | 5.7 | 0.16 | 1.6 | 1.9 | 0.3 | 19 |

[a]Data (% dose g$^{-1}$) normalized to 25 g body wt, purification carried out by HPLC using Zorbax GF-250 column; n = 5.
[b]Percent injected dose retained.

TABLE 12

Tumor (T)/Tissue Ratios of Cobalt-57 Labeled
Anti-CEA F(ab')$_2$ Conjugates in Nude Tumor Mice[a]

| Bifunctional Chelating Agent | Time (H) | T/ Blood | T/ Liver | T/ Kidney | T/ Bone |
|---|---|---|---|---|---|
| 4-ICE | 24 | 4.4 | 3.0 | 2.1 | 15 |
|  | 96 | 44 | 4.1 | 3.8 | 20 |
| 4-BACE | 24 | 4.0 | 2.0 | 1.7 | 13 |
|  | 96 | 36 | 3.6 | 3.1 | 18 |

[a]n = 5

TABLE 13

Tissue Distribution in Nude Tumor Mice of 17-1A IgG Conjugates Labeled with $^{88}Y^a$

| Bifunctional Chelating Agent | Time (H) | Tumor | Blood | Liver | Kidney | Bone | Whole[b] Body |
|---|---|---|---|---|---|---|---|
| 4-ICE | 24 | 7.0 | 9.9 | 6.4 | 4.7 | 8.5 | 87 |
|  | 96 | 6.4 | 2.8 | 4.7 | 3.7 | 13.3 | 72 |
| DTPADA | 24 | 5.0 | 6.4 | 16.1 | 3.4 | 10.4 | 90 |
|  | 96 | 3.6 | 1.7 | 11.3 | 2.4 | 10.6 | 67 |

[a]Data (% dose $g^{-1}$) normalized to 25 g body wt; purification carried out by HPLC using Zorbax GF-250 column; n = 5.
[b]Percent of injected dose retained.

TABLE 14

Tissue Distribution in Nude Tumor Mice of Anti-CEA F(ab')$_2$ Conjugates Labeled with $^{203}Pb^a$

| Bifunctional Chelating Agent | Time (H) | Tumor | Blood | Liver | Kidney | Bone | Whole[b] Body |
|---|---|---|---|---|---|---|---|
| 4-ICE | 24 | 7.7 | 4.7 | 8.4 | 19.1 | 7.6 | 76 |
|  | 96 | 2.2 | 1.6 | 3.0 | 8.1 | 11 | 46 |

[a]Data (% dose $g^{-1}$) normalized to 25 g body wt; purification carried out by HPLC using Zorbax GF-250 column; n = 5.
[b]Percent of injected dose retained.

EXAMPLE 1

Production of Trans-1,2-diamino-4-acetamido cyclohexane-N,N,N',N'-tetra ethyl acetate

METHOD ONE

The starting material in this synthesis, trans-1,2-diaminocyclohex-4-ene dihydrochloride was prepared by a modification of the procedure of Witiak et al. [J. Med. Chem. 30, 1327 (1987)]. Freshly distilled fumaryl chloride (25 g 163 mmoles) was dissolved in 150 ml dry THF in a 250 ml round bottom flask with a dry ice condenser. The solution was cooled to −50° C. (dry ice/acetonitrile) under nitrogen. Approximately 30 ml butadiene was condensed into the flask. The dry ice condenser and bath were removed. As the flask warmed to room temperature a rigorous exothermic reaction began and insued for approximately 45 min. The reaction was allowed to stand at room temperature for 2 hours and then was concentrated under vacuum to give 34.5 g of a colorless liquid (~100%) of trans-4-cyclohexene-1,2-dicarbonyl dichloride. Next the trans-4-cyclohexene-1,2-dicarbonyl dichloride was dissolved in 300 ml THF cooled to 0° C. under N$_2$. To this was added (50 ml) (377 mmol) trimethylsilylazide. The reaction was then slowly heated to reflux, refluxed for 4 hours, then cooled to room temperature. To this was cautiously added dropwise 55 ml of concentrated HCl. After 30 min. the resulting white precipitate was filtered, washed with acetone and dried to give 13.7 g (45%) of trans-1,2-diaminocyclohex-4-ene dihydrochloride mp>340° C. The filtrate was saved and an additional 7.8 g (26%) of product precipitated over a period of three weeks.

Next, 14.0 g (76 mmol) of trans-1,2-diaminocyclohex-4-ene dihydrochloride was dissolved in 159 ml of 7M KOH (1.1 moles). To this was added in three portion over 3 h 64 g (460 mmole) of bromoacetic acid. The reaction was stirred at 45° C. for 4 days and each day 10 g of bromoacetic acid was added. 7M KOH was added as needed to keep the pH>10. The reaction was acidified by the addition of concentrated HBr and the resulting precipitate was filtered, washed with cold water followed by acetone, and dried under vacuum to give 16.7 g (64%) of trans-1,2-diaminocyclohex-4-ene-N,N,N',N'-tetraacetic acid mp 267°−269° C.

To a suspension of 2.0 g (5.8 mmol) trans-1,2-diaminocyclohex-4-ene-N,N,N',N'-tetraacetic acid in 75 ml absolute ethanol is added 10 ml of boron tri-fluoride etherate. This was gently refluxed under N$_2$ for 15 hours during which time all the solid dissolved. The reaction was then cooled to room temperature and partioned between 100 ml water and 100 ml ethylacetate. The layers were separated and the aqueous layer further extracted with 2×100 ml ethylacetate. The organic layers were combined, washed with a solution of saturated sodium chloride, dried over magnesium sulfate, and concentrated under vacuum to an off white solid. This was recrystallized from an ethylacetate ethylether mixture to give 2.2 g (84%) of trans-1,2-diaminocyclohex-4-ene-N,N,N',N'-tetraethylacetate as a white powder mp 111°−113° C.

A mercuration-amidation step was then carried out using the conditions of Brown and Kurek [JACS: 91,5647 (1969)]. A stirred suspension of 9.5 g (2.9 mmol) anhydrous mercuric nitrate Hg(NO$_3$)$_2$ (Fluka) in 50 ml dry acetonitrile was cooled to 15°−20° C. under N$_2$. To this was added in small portions over 30 min. 2.7 g (5.9 mmol) trans-1,2-diaminocyclohex-4-ene-N,N,N',N'-tetraethylacetate. The reaction was allowed to warm to room temperature and stirred an additional 4 hours. The reaction was concentrated to 15−20 ml, cooled to 0°−2° C. and quenched by the addition of 88 ml 3M NaOH and 88 ml of 0.5M NaBH$_4$ in 3M NaOH. This was stired for 30 min. and then 15 g NaCl was added and the slurry stirred for another 30 min. The slurry was filtered through a Celite plug and the celite washed with 300 ml methylene chloride. The organic layer was separated and the aqueous layer extracted with 150 ml $CH_2Cl_2$. The organic layers were combined, dried over $MgSO_4$ and concentrated to give a sticky solid which was purified by column chromatography (silica gel, 15/1 $CH_2Cl_2$/methanol) to give 0.9 g (29%) of trans-1,2-diamino-4-acetamido-cyclohexane-N,N,N,N-tetraethylacetate as a yellow oil.

METHOD 2

To a solution of 28.3 ml (162 mmol) diisopropylthylamine dissolved in 200 ml dry DMF was added 10.0 g (54 mmol) trans-1,2-diaminocyclohex-4-enedihydrochloride under $N_2$. To this was slowly added 29.8 ml di-tert-butyl dicarbonate. This was stirred at room temperature overnight, concentrated to a solid and was partitioned between 200 ml $H_2O$ and 400 ml ethylacetate. The layers were separated and the aqueous layer was extracted with an additional 200 ml ethylacetate. The ethylacetate layers were combined, dried over $MgSO_4$, concentrated to an off white solid which was recrystallized from $Et_2O$/EtAc to give 10.7 g (64%) of N,N'-(t-butoxycarbonyl)-trans-1,2-diaminocyclohex-4-ene as a white solid mp 143°–145° C. The filtrate was concentrated and purified by column chromatography (silica gel, 6/1 Hexane/Ethylacetate) to give an additional 4.5 g of a white solid (27%) mp 141°–144° C. Total yield 91%.

A suspension of 5.0 g (15.4 mmol) $Hg(NO_3)_2$ in 50 ml dry acetonitrile was cooled to 15°–20° C. under $N_2$. To this was added in small portions over one hour 3.4 g (10.3 mmol) N,N'-(t-butoxycarbonyl)-trans-1,2-diaminocyclohexane. The reaction was allowed to warm to room temperature and stirred for 4 hours. The reaction was concentrated to about 20 ml, cooled to 0°–2° C. and quenched by the addition of 35 ml 3M NaOH and 35 ml of 0.5M $NaBH_4$ in 3M NaOH. This was stirred for 30 min., then 10 g of NaCl was added and the slurry stirred for another 30 min. The slurry was filtered through a Celite plug and the plug was washed with 200 ml $CH_2Cl_2$. The organic layer was separated and the aqueous layer washed with 100 ml $CH_2Cl_2$. The organic layers were combined, dried over $MgSO_4$ and concentrated to a sticky solid. This was purified by column chromatography (silica gel, 20/1 $CH_2Cl_2$/methanol) to give 2.7 g (73%) of N,N'-(trans-1,2-di(-t-butoxycarbonyl))-4-acetamidyl-cyclohexane as a waxy solid.

To a solution of 6.2 g (17.4 mmol) N,N'-(trans-1,2-di(-t-butoxy-carbonyl))-4-acetamidyl-cyclohexane dissolved in 100 ml acetone cooled to 0°–2° C. was added 80 ml 3M HCl. This was warmed to room temperature, stirred at room temperature overnight, and evaporated to dryness under reduced pressure. The residue was further dried by redissolving in absolute ethanol and evaporating to dryness. This was repeated twice more. To the residue was then added 30 ml $H_2O$ and 5.8 g (69 mmol) $NaHCO_3$ (pH of solution was 8). To the reaction was then added 250 ml DMF, 30 ml $H_2O$, 12 g $NaHCO_3$ and 23 ml (210 mmol) ethyl bromoacetate. The reaction was stirred at room temperature for 7 days, filtered, and the solid was washed with DMF. The filtrate was collected and concentrated under reduced pressure. The resulting slurry was partitioned between 150 ml $CH_2Cl_2$ and 150 ml $H_2O$. The $CH_2Cl_2$ layer was removed and the aqueous layer extracted with an additional 200 ml $CH_2Cl_2$. The organic layers were combined, dried over $MgSO_4$, and concentrated to give 9.2 g of a thick orange oil. This oil was purified by column chromatography (silica gel, 5/2 EtAc/$CH_2Cl_2$) to give 7.0 g (70%) of trans-1,2-diamino-4-acetamido-cyclohexane-N,N,N',N'-tetraethylacetate as a yellow oil.

To a solution of 5.8 g (11.3 mmol) trans-1,2-diamino-4-acetamido-cyclohexane-N,N,N',N'-tetra ethylacetate dissolved in 30 ml ethanol was added 150 ml 3M HCl. This was heated to 100° C. in an open round bottom flask overnight. An additional 50 ml 3M HCl was added to the reaction, the flask was equipped with a reflux condenser, and the reflux continued an additional 24H. Then the reaction was concentrated to a solid residue, redissolved in a methanol/ethanol mixture and evaporated to dryness. This was repeated twice more. The residue was dissolved in 20 ml methanol and the tetra acid was precipitated by the dropwise addition of the methanolic solution to 400 ml acetone. The resulting suspension was stirred for 5 days, filtered, washed with acetone and dried under vacuum at 100° C. to give 4.33 g (96%) of trans-1,2-di[bis(carboxymethyl)amino]-4-amino-cyclohexane hydrochloride as an off white solid mp 225° C.

EXAMPLE 2

Formation of Trans-1,2-di[bis(carboxymethyl)amino]-4-isothiocyanato-cyclohexane dilithium salt To 8.5 ml of 0.595M LiOH (5 mmol) was added 0.4 g (1 mmol) trans-1,2-di[bis(carboxymethyl)amino]-4-amino-cyclohexane hydrochloride. This was stirred for one hour, then concentrated to a sticky solid. To the residue was reconstituted in 40 ml methanol and reevaporated. This was repeated twice more. The white powder was dried under vacuum overnight. This was dissolved in 15 ml (dry methanol) under $N_2$. To this was added 1.5 ml of 0.66M thiophosgene in $CH_2Cl_2$ (1 mmol). After stirring for 1 h., the flourescamine test for primary amines was still slightly positive so an additional 0.5 ml of 0.66M thiophosgene in $CH_2Cl_2$ was added. One hour later the flourescamine test was negative and the reaction was concentrated to dryness. The resulting yellow solid was dissolved in 3 ml dry methanol and the product precipitated by the addition of 100 ml acetone. The precipitate was collected, washed with acetone and dried under vacuum to give 0.39 g (94%) of trans-1,2-di[bis(carboxymethyl)amino]-4-isothiocyanato-cyclohexane dilithium salt, as a tan powder.

EXAMPLE 3

Formation of Trans-1,2-di[bis(carboxymethyl)amino]-4-bromoacetamido-cyclohexane

To 50 ml of dry DMF was added 1.3 ml diisopropylethylamine (7.6 mmol) and 1.8 g (7.6 mmol) N-succinimidyl-bromoacetate [Mease et al., U.S. Pat. No. 5,089,663]. To this stirred solution under $N_2$ was added 0.5 g (1.26 mmol) trans-1,2-di[bis(carboxymethyl)amino]-4-aminocyclohexane hydrochloride in small portions as a solid over a period of 18 hours. The reaction was stirred an additional 24 hours. At this time the flourescamine test for primary amines was negative. The reaction mixture was concentrated to a thick oil, dissolved in 5 ml of methanol and the product precipitated by the addition of 400 ml of acetone to give 0.2 g (33%) of trans-1,2-di[bis(carboxymethyl)amino]-4-bromoacetamido-cyclohexane as a brown solid.

EXAMPLE 4

Antibody Conjugation Using 4-ICE/4-BACE

To either 17-1A IgG or anti-CEA F(ab')$_2$ antibody in 0.1N sodium bicarbonate at an antibody concentration of 20 mg/ml was added 4-ICE/4-BACE in DMSO at a molar ratio of 4-ICE/4-BACE to antibody of 25/1. These solutions were allowed to incubate at 37° C. overnight. The uncoupled ligand was removed using a Centricon C-30 centrifugation/filtration device. The average number of chelates per antibody was determined by the radiocobalt assay of Meares et al. [Anal. Biochem. 142, 68 (1984)] to be 2 for both 4-ICE and 4-BACE conjugates.

EXAMPLE 5

$^{111}$In-17-1A IgG Immunoconjugate Biodistribution

To the 17-1A IgG antibody in 0.1N sodium bicarbonate at an antibody concentration of 20 mg/ml was added CDTAMA in DMSO at a molar ratio of CDTAMA/antibody of 10/1. This solution was allowed to incubate at 4° C. overnight. The uncoupled CDTA was removed using a Centricon C-30 centrifugation/filtration device. DTPADA was conjugated using the procedure of Hnatowich et al. J. Immunol Meth 65, 147 (1983). 4-ICE and 4-BACE were conjugated as described in the previous example. The immunoconjugates were labeled with $^{111}$InCl$_3$ (Nordion, as a 0.05M HCl solution) in an acetate (0.1M)/citrate (0.02M) buffer, pH 5 and purified by HPLC on a Zorbax GF-250 column using 0.2M, pH 7 phosphate buffer. Only monomeric antibody (high molecular weight material was only prepared when DTPADA was used) was collected and used in the biodistribution. 2 µCi/25 µg antibody was injected intravenously (tail vein) in normal or human colon ca (SW948) xenografted nude mice. The distribution in normal mice and tumor mice at 24 and 96H is shown in Tables 1 and 2, respectively.

EXAMPLE 6

$^{111}$In-Anti-CEA F(ab')$_2$-Immunoconjugate Biodistribution

In this example the biodistribution of $^{111}$In labeled 4-ICE, 4-BACE, and DTPA-anti-CEA F(ab')$_2$ conjugates were competed. DTPADA was conjugated using the procedure of Hnatowich et al. J. Immunol. Meth. 65, 147 (1983). 4-ICE and 4-BACE were conjugated as previously described. The average number of chelates per antibody were determined by the radiocobalt assay of Meares et al. to be 3, 2, and 2 for the DTPADA, 4-ICE, and 4-BACE conjugates respectively. The preparations were labeled with $^{111}$In and purified by HPLC as described in an earlier example. The labeled anti-CEA preparations were injected intravenously (tail vein) into LS 174T xenografted nude mice. The distributions at 24 and 96H are shown in Table 4.

EXAMPLE 7

$^{47}$Sc-17-1A IgG Immunoconjugate Biodistribution

In this example the biodistribution of $^{47}$Sc labeled 4-ICE, CDTAMA, and DTPADA-17-1A IgG conjugates were compared in normal mice and $^{47}$Sc labeled 4-ICE and DTPADA-17-1A IgG conjugates were compared in human colon ca SW948 xenografted nude mice. 4-ICE, CDTAMA, and DTPADA 17-1A conjugates were prepared as in previous examples. The average number of chelates per antibody was determined by the radiocobalt assay of Meares et al. to be 2, 2, and 3 for the 4-ICE, CDTAMA, and DTPADA conjugates respectively. $^{47}$Sc was produced with the fast neutron reaction $^{47}$Ti(n,p)$^{47}$Sc at the BNL High Flux Beam Reactor (HFBR). The scandium was separated from the $^{47}$TiO$_2$ target using cation exchange chromatography using first an elution of dilute HCl followed by a solution of ammonium acetate [Kolsky et al. J. Nucl. Med. 32, 945 (1991)]. The ammonium acetate solution was evaporated to dryness and the $^{47}$Sc reconstituted in 0.05M HCl.

The immunoconjugates were labeled with $^{47}$ScCl$_3$ in an acetate (0.1M)/citrate (0.02M) buffer, pH 5, and purified by HPLC on a Zorbax GF-250 column as described earlier. The labeled preparations were injected intravenously (tail vein) into LS 174T xenografted nude mice and normal mice. The distributions in normal and tumor mice at 24 and 96H am shown in Tables 6 and 7, respectively.

EXAMPLE 8

$^{57}$Co-17-1A IgG-Immunoconjugate Biodistribution

In this example, the biodistribution of $^{57}$Co labeled 4-ICE and 4-BACE-17-1A IgG conjugates in SW948 xenografted nude mice were compared with CDTAMA- and DTPADA-17-1A distributions previously described [Mease et al. U.S. Pat. No. 5,089,663]. 4-ICE and 4-BACE were conjugated as described in an earlier example. The average number of chelates per antibody was determined by the radiocobalt assay of Meares et al. to be 2 for both ligands. The immunoconjugates were labeled with $^{57}$CoCl$_2$ in a 0.02M citrate buffer at a protein concentration of 20 mg/ml. The preparations were purified by HPLC on a Zorbax GF-250 column as previously described. The labeled immunoconjugates were injected intravenously (tail vein) into human colon ca (SW948) xenografted nude mice. The distributions at 24 and 96 Hrs are given in Table 9.

EXAMPLE 9

$^{57}$Co -Anti-CEA F(ab')$_2$ Immunoconjugate Biodistribution

4-ICE and 4-BACE were conjugated to anti-CEA F(ab')$_2$ as described above. The average number of chelates per antibody were determined by the radiocobalt assay of Meares et al. to be 2 for both preparations. The preparations were labeled with $^{57}$Co and purified by HPLC as previously described. The labeled anti-CEA preparations were injected intravenously (tail vein) into LS 174T xenografted nude mice. The biodistributions at 24 and 96H are shown in Table 11.

EXAMPLE 10

$^{88}$Y-17-1A IgG Immunoconjugate Biodistribution

In this example, the biodistribution of $^{88}$Y labeled 4-ICE and DTPADA-17-1A conjugates were compared in human colon ca (SW948) xenografted nude mice. The 4-ICE and DTPADA-17-1A conjugates were prepared as described above. The average number of ligands per antibody as determined by the radiocobalt assay of Meares, et al. was 2 and 3 for 4-ICE and DTPADA conjugates, respectively. Yttrium-88 was purchased from Los Alamos National Laboratory as $^{88}$YCl$_3$ in 6M HCl. This was evaporated to dryness and reconstituted in 0.05M HCl. The conjugates were labeled with $^{88}$Y in a buffer that was 0.04M NaHCO$_3$ and 0.2M acetate and purified by HPLC as previously described. The labeled 17-1A was injected intravenously (tail vein) into human colon ca (SW 948) xenografted nude mice. The distributions at 24 and 96H are shown in Table 13.

EXAMPLE 11

$^{203}$Pb-17-1A IgG Immunoconjugate Biodistribution

4-ICE was conjugated to 17-1A as previously described, labeled with $^{203}$Pb at pH 8 in 0.02M citrate and 0.1M NaHCO$_3$, and purified by HPLC as previously described. The labeled 17-1A conjugate, was injected intravenously (tail vein) into human colon ca (SW 948) xenografted nude mice. The distributions at 24 and 96H are shown in Table 14. From these results, it can be concluded that the metal binding region of the functionalized CDTA conjugates of the present invention works best with metals which prefer six coordinating groups.

We claim:

1. A diagnostic method comprising the steps of:
   conjugating a compound selected from the group consisting of 4-amino-trans-1,2-diaminocyclohexane-N,N,N', N'-tetraacetic acid, 4-isothiocyanato-trans-1,2-diaminocyclohexane-N,N,N',N'-tetraacetic acid, and trans-1,2-di[bis(carboxymethyl)amino]-4-haloacetamido-cyclohexane with an antibody or a bioactive peptide and a radioactive metal to form a radioimmunoconjugate;
   administering an imaging effective amount of said radioimmunoconjugate to a mammal wherein said radioimmunoconjugate selectively localizes in a target region of said mammal; and
   detecting radiation emitted by said radioimmunoconjugate.

2. A diagnostic method according to claim 1 wherein said metal is $^{111}$In or $^{47}$Sc and said detecting step comprises planar imaging.

3. A diagnostic method according to claim 1 wherein said metal is $^{111}$In or $^{47}$Sc and said detecting step comprises SPECT imaging.

4. A diagnostic method according to claim 1 wherein said metal is $^{55}$Co and said detecting step comprises PET imaging.

5. A diagnostic method according to claim 1 wherein said trans-1,2-di[bis(carboxymethyl)amino]-4-haloacetamido-cyclohexane is trans-1,2-di[bis(carboxymethyl)amino]-4-bromoacetamido-cyclohexane.

6. A diagnostic method according to claim 1 wherein said trans-1,2-di[bis(carboxymethyl)amino]-4-haloacetamido-cyclohexane is trans-1,2-di[bis(carboxymethyl)amino]-4-chloroacetamido-cyclohexane.

7. A diagnostic method according to claim 1 wherein said trans-1,2-di[bis(carboxymethyl)amino]-4-haloacetamido-cyclohexane is trans-1,2-di[bis(carboxymethyl)amino]-4-iodoacetamido-cyclohexane.

8. The diagnostic method of claim 1, wherein said antibody includes an antibody fragment.

9. A diagnostic method comprising the steps of:
   providing trans-1,2-di[bis(carboxymethyl)amino]-4-amino-cyclohexane hydrochloride;
   contacting said trans-1,2-di[bis(carboxymethyl)amino]-4-amino-cyclohexane hydrochloride with LiOH to form a first solution;
   concentrating said first solution to a salt and reconstituting said salt in methanol to form a reconstituted solution;
   contacting said reconstituted solution with thiophosgene in CH$_2$Cl$_2$ to form 4-isothiocyanato-trans-1,2-diamino cyclohexane-N, N, N', N'-tetra acetic acid;
   conjugating said 4-isothiocyanato-trans-1,2-diamino cyclohexane-N, N, N', N'-tetra acetic acid with an antibody or bioactive peptide and a radioactive metal to form a radioimmunoconjugate;
   administering an imaging effective amount of said radioimmunoconjugate to a mammal wherein said conjugate selectively localizes in a target region of said mammal; and
   detecting radiation emitted by said radioimmunoconjugate.

10. A method for radioimmunotherapy of cancer cells comprising the steps of:
    providing trans-1,2-di[bis(carboxymethyl)amino]-4-amino-cyclohexane hydrochloride;
    contacting said trans-1,2-di[bis(carboxymethyl)amino]-4-amino-cyclohexane hydrochloride with LiOH to form a first solution;
    concentrating said first solution to a salt and reconstituting said salt in methanol to form a reconstituted solution;
    contacting said reconstituted solution with thiophosgene in CH$_2$Cl$_2$ to form 4-isothiocyanato-trans-1,2-diamino cyclohexane-N, N, N', N'-tetra acetic acid;
    conjugating said 4-isothiocyanato-trans-1,2-diamino cyclohexane-N, N, N', N'-tetra acetic acid with an antibody or bioactive peptide and a beta emitting radioactive metal to form a radioimmunoconjugate;
    administering an imaging effective amount of said radioimmunoconjugate to a mammal wherein said radioimmunoconjugate selectively localizes in a target region containing said cancer cells of said mammal.

11. The method of claim 10, wherein said cancer cells are treated by a beta emitting radioactive metal selected from the group consisting of $^{47}$Sc and $^{88}$Y.

12. The method of claim 10 wherein said cancer cells are treated by Y$^{90}$.

13. A diagnostic method comprising the steps of:
    conjugating trans-1,2-di[bis(carboxymethyl)amino]-4-haloacetamido-cyclohexane with an antibody or bioactive peptide and a radioactive metal to form a radioimmunoconjugate;
    administering an imaging effective amount of said radioimmunoconjugate to a mammal wherein said radioimmunoconjugate selectively localizes in a target region of said mammal; and
    detecting radiation emitted by said radioimmunoconjugate.

14. The diagnostic method of claim 13, wherein said trans-1,2-di[bis(carboxymethyl)amino]-4-haloacetamido-cyclohexane is selected from the group consisting of trans-1,2-di[bis(carboxymethyl)amino]-4-bromoacetacetamido-cyclohexane, trans-1,2-di[bis(carboxymethyl)amino]-4-chloroacetamido-cyclohexane, trans-1,2-di[bis(carboxymethyl)amino]-4-iodoacetamido-cyclohexane.

15. A diagnostic method comprising the steps of:
    contacting a compound selected from the group consisting of 4-amino-trans-1,2-diaminocyclohexane-N,N,N',N'-tetraacetic acid, 4-isothiocyanato-trans-1,2-diaminocyclohexane-N,N,N',N'-tetraacetic acid, and trans-1,2-di[bis(carboxymethyl)amino]-4-haloacetamido-cyclohexane with an antibody or bioactive peptide in dimethyl sulfoxide to form an immunoconjugate;
    labeling said immunoconjugate with a radioactive metal to form a radioimmunoconjugate;
    administering an imaging effective amount of said radioimmunoconjugate to a mammal wherein said radioimmunoconjugate selectively localizes in a target region on said mammal; and
    detecting radiation emitted by said radioimmunoconjugate.

16. The diagnostic method of claim 15, wherein said trans-1,2-di[bis(carboxymehtyl)amino]-4-4haloacetamido-cyclohexane is selected from the group consisting of trans- 1,2-di[bis(carboxymethyl)amino]-4-bromoacetacetamido-cyclohexane, trans-1,2-di[bis(carboxymehtyl)amino]-4-chloroacetamido-cyclohexane, trans-1,2-di[bis(carboxymethyl)amino]-4-iodoacetamido-cyclohexane.

17. A delivery system for radioimmunotherapy which comprises:

a chelating compound selected from the group consisting of 4-amino-trans-1,2-diaminocyclohexane-N,N,N,N'-tetraacetic acid, 4-isothiocyanato-trans-1,2-diaminocyclohexane-N,N,N'N'-tetraacetic acid, and trans-1,2-di[bis(carboxymethyl)amino]-4-haloacetamido-cyclohexane;

an antibody or bioactive peptide and a beta emitting radioactive metal conjugated to said chelating compound, wherein said chelating compound conjugates with said antibody or said bioactive peptide at the 4-substituted position.

* * * * *